United States Patent [19]

Montgomery

[11] 4,293,728

[45] Oct. 6, 1981

[54] PRETREATMENT OF BUTENE-1 IN ISOMERIZATION OF IT TO BUTENE-2

[75] Inventor: Dean P. Montgomery, Bartlesville, Okla.

[73] Assignee: Phillips Petroleum Co., Bartlesville, Okla.

[21] Appl. No.: 135,606

[22] Filed: Mar. 31, 1980

[51] Int. Cl.$^3$ ............................................... C07C 5/23
[52] U.S. Cl. ...................................... 585/670; 585/852
[58] Field of Search .................................. 585/852, 670

[56] References Cited

U.S. PATENT DOCUMENTS

| | | | |
|---|---|---|---|
| 2,924,629 | 2/1960 | Donaldson | 585/482 |
| 3,110,566 | 11/1963 | Giammarco | 423/578 |
| 3,531,542 | 9/1968 | Myers et al. | 585/670 |

*Primary Examiner*—Curtis R. Davis

[57] ABSTRACT

Prior to subjecting a butene-1 containing stream isomerization to produce butene-2 in the presence of a catalyst, e.g., a palladium catalyst, the feedstream is subjected to pretreatment in the presence of a contact mass adapted to remove under pretreatment conditions from the feedstream impurities which adversely affect the catalyst, e.g., sulfur and arsenic.

4 Claims, No Drawings

PRETREATMENT OF BUTENE-1 IN ISOMERIZATION OF IT TO BUTENE-2

BRIEF SUMMARY OF THE INVENTION

Isomerization of butene-1 to butene-2 is considerably improved by passing hydrocarbon feed to an alumina guard bed or chamber and then to a catalyst bed comprising a supported noble metal of Group VIII such as palladium/alumina.

DETAILED DESCRIPTION

In one of its aspects this invention relates to the isomerization of an olefin. In a more specific aspect, the invention relates to the isomerization of butene-1 to butene-2. More specifically, still, the invention relates to a process of isomerizing butene-1 to butene-2 in which improved ratios of butene-1/butene-2 are obtained.

In one of its concepts the invention provides a process for the isomerization of butene-1 to butene-2 which comprises subjecting the feedstream, which ordinarily contains impurities which will interfere with the activity of the ensuing isomerization catalyst, such as, shortening of, reduction of, or increase of catalyst life, isomerization effectiveness, the amount of undesirable side reactions or by-product to a pretreatment to remove such impurities therefrom as by contacting the feedstream with a bed of material which will accomplish such removal. In another of its concepts the invention provides a process as described in which a guard or pretreatment bed comprising alumina or activated alumina is employed to treat the feed prior to subjecting it to isomerization conditions. In a further concept of the invention it provides a process in which, in lieu of the alumina a molecular sieve (silica-alumina) is employed. In the now preferred concept of the invention, the pretreatment is accomplished employing a combination of activated alumina and activated carbon.

I have now discovered that the pretreatment as herein described of a butene-1 containing stream, containing minor quantities of other materials, e.g., butene-2, will significantly increase the butene-1 to butene-2 conversion ratio.

The pretreatment removes impurities such as sulfur and arsenic which are present in the feedstream.

It is an object of this invention to provide a process for the isomerization of isomerizable olefins having from 4 to about 8 carbon atoms per molecule. Some examples of these are butene-1, butene-2, pentene-1, hexane-2, 4-methylhexene-1, 5-methyloctane-1, and the like and mixtures thereof. It is a further object of this invention to provide a process for the improved isomerization of butene-1 to butene-2.

By isomerizable olefins is meant olefins whose double bonds can be shifted within the molecule without skeletal change. Thus neohexene which has quatenary carbon atoms blocking the movement of double bonds is not ordinarily isomerizable.

Other aspects, concepts, objects and several advantages of the invention are apparent from a study of this disclosure and the appended claims.

According to the present invention an olefin, e.g., butene-1, is isomerized, e.g., to butene-2, by subjecting the feedstream to a pretreatment with at least one of an activated alumina suited to remove sulfur and arsenic from said stream, and then subjecting the thus pretreated stream to an isomerization catalyst, e.g., a palladium isomerization catalyst, under isomerization conditions.

It is known that a butene mixture containing butene-1 is difficult to separate in a fractionation tower because of close boiling points. Butene-2, however, has a higher boiling point than butene-1, about 7° C. Consequently, a fractionation process for such mixture including an isomerization step which first converts butene-1 to butene-2 before the fractionation step will considerably facilitate the separation. Also, butene-2 is sometimes more advantageous as a charging stock than is butene-1. For example, at least one process which has been disclosed advantageously performs alkylation of an isoparaffin employing in the olefin charging the stock of butene-2.

It was found that the isomerization of butene-1 to butene-2 improved significantly by passing the butene-1 containing feed to an alumina guard bed and then to a CCI C-31-1 palladium catalyst bed having an inlet temperature of 75°–400° F., at a pressure of 5–1000 psig and at a space rate of 50–3000 GHSV, the feed containing 3 moles of $H_2$ per 100 moles of hydrocarbons.

After leaving the reaction zone, the isomerized mixture can be separated by conventional means such as by fractionation or can be subjected to additional chemical conversions as desired.

The aluminas which are applicable for the pretreatment step of the present invention are the conventional adsorbent or catalytic grades of materials widely known for use in chemical conversions, particularly in hydrocarbon processes. There are amorphous, activated aluminas, frequently gamma or eta form, of relatively high surface area. These can be of any conventional particulate size or form such as granules, spheres, pellets, tablets, extrudates, powder, etc., and will have a surface area of at least about 1 $m^2/g$ and usually more than about 100 $m^2/g$. Before use they are activated by a conventional heat treatment to drive out adsorbed water or other volatiles.

The pretreatment can be carried out in an apparatus by which a liquid or vaporous feed stream is efficiently contacted with a solid adsorbent such as alumina. Apparently, such as that used for fixed bed, moving bed, or fluidized bed can be effectively used in this invention.

The isomerization catalysts applicable for use in the present invention are those containing the noble metals of Group VIII of the Periodic Table of Elements. These include ruthenium, rhodium, palladium, osmium, iridium, and platinum. These are preferably associated with a suitable catalyst support material such as alumina, glass beads, carbon, etc.

A particularly effective catalyst, especially when used to isomerize olefinic $C_4$ refinery streams, is palladium on alumina. This is a well known catalytic material which contains from about 0.005 to about 1.0 weight percent palladium, preferably 0.01 to 0.1. It has a surface area in excess of 200 $m^2/g$, preferably in excess of 300 $m^2/g$. A specific commercial catalyst of this type which is very useful is a Catalyst and Chemicals Incorporated catalyst referred to as C-31-1 which contains about 0.05 weight percent Pd on alumina and which has a surface area of about 340 $m^2/g$.

Although the pretreatment of the isomerizable feed stream with alumina is effective in producing the desired improved results of longer catalyst life and greater isomerization effectiveness (nearer equilibrium conversions), contact with other pretreatment materials can be employed if desired in addition to contact with the alumina. For example, an alumina bed can be preceded or followed by other conventional guard chamber beds such as mole sieves, silica gel, activated carbon, activated clay, zinc oxide, etc. These additional treatment beds may still further extend the life and effectiveness of the alumina bed, but are not considered absolutely necessary to obtain the satisfactory level of operation brought about by the use of the alumina bed itself.

SPECIFIC EXAMPLES

Example 1 (Invention Run)

A $C_4$ refinery stream, more specifically a heart cut of a $C_4$ stream normally used as an alkylation feed, was isomerized according to the process of the present invention. During the period of this invention run and other comparison runs, the composition of the feed, contained in four separate cylinders, varied very little as shown below.

| $C_4$ Refinery Stream Analysis | |
|---|---|
| Component | Mole % |
| $C_3$ | 3.34–4.56 |
| $C_3^=$ | 4.60–5.93 |
| $iC_4$ | 30.38–31.17 |
| $nC_4$ | 6.11–7.04 |
| $C_4^= - 1$ | 21.18–21.94 |
| $i\text{-}C_4^=$ | 24.21–25.39 |
| $t\text{-}C_4^= - 2$ | 4.42–5.09 |
| $c\text{-}C_4^= - 2$ | 1.15–1.40 |
| $C_4^{==}$ | 1.05–1.78 |
| $iC_5$ | (about 0.2 wt. %) |

The above described feed, having an initial $C_4^=\text{-}2/C_4^=\text{-}1$ ratio of about 0.3, was sequentially passed through an activated alumina bed, an activated carbon bed (later found unnecessary) and a catalyst chamber containing a $Pd/Al_2O_3$ isomerization catalyst. The activated alumina was a commercial alumina (Harshaw Alumina, AL-0108-T) in the form of ⅛ in. tablets. The activated carbon was a commercial (Darco LIPT, DXL-0-4652) 12 mesh material which was low iron and post-treated at high temperature in an oxygen-free environment. The isomerization catalyst was the previously-described 0.05 wt. % Pd on alumina (Catalyst and Chemicals Inc., C-31-1) of 3–10 mesh size.

The conditions for the 3 contacting zones were:

| | Temp. °F. | Press. psig | Space Rate GHSV | Hydrogen Moles/100 Moles Feed |
|---|---|---|---|---|
| Alumina bed | ≦190 | 130 | 117 | 0 |
| Carbon bed | 190 | 130 | 1560 | 0 |
| $Pd/Al_2O_3$ bed | 300 | 130 | 260 | 3 |

The effluent from this system was periodically sampled and analyzed for its efficiency to convert butene-1 to butene-2. The table below shows this efficiency in terms of the $C_4^=\text{-}2/C_4^=\text{-}1$ ratio over the length of a 175 hr. run.

For purposes of comparison another run was similarly carried out but without any pretreatment beds. The results of this run are also shown below.

| $Al_2O_3$ Pretreatment | | No Pretreatment | |
|---|---|---|---|
| Time on Stream Hrs. | Isom. Eff. $C_4^= - 2/C_4^= - 1$ Ratio | Time on Stream Hrs. | Isom. Eff. $C_4^= - 2/C_4^= - 1$ Ratio |
| 6.21 | 11.9 | 1.38 | 6.6 |
| 10.00 | 9.6 | 6.43 | 6.7 |
| 14.00 | 10.9 | 9.15 | 6.11 |
| 19.30 | 11.4 | 14.00 | 8.6 |
| 20.00 | 12.0 | 18.47 | 4.9 |
| 25.25 | 12.3 | 20.00 | 3.47 |
| 29.48 | 11.8 | 21.16 | 3.5 |
| 41.56 | 11.8 | 25.47 | 3.3 |
| 45.25 | 11.95 | 29.23 | 3.0 |
| 109.55 | 10.18 | 41.32 | 2.96 |
| 114.43 | 11.60 | 45.49 | 2.87 |
| 128.53 | 9.87 | 61.19 | 2.9 |
| 170.10 | 9.33 | 80.36 | 2.2 |
| 175.49 | 9.76 | | |

The data in the table above show that the butene-1 in the feed stream, which had an original butene-2/butene-1 ratio of about 0.3, was very substantially isomerized as evidenced by the relatively high ratio of about 10–12 for the first 115 hours and of about 10 up to 175 hours.

In contrast the run with no pretreatment did not readily isomerize butene-1. The butene-2/butene-1 ratio was relatively low and declined rapidly to an even lower value after a relatively short time.

Example 2 (Comparison Run)

This run illustrates the ineffectiveness of activated carbon when used as the sole pretreating agent for the isomerization of butene-1 in the same $C_4$ refinery cut described in example 1. The $Pd/Al_2O_3$ catalyst was the same as described in example 1; the activated carbon was Darco 12×20 mesh, purged with feedstock for 20 hours at 120° F. and 78 psig. The conditions were as follows.

| | Temp. °F. | Press. psig | Space Rate GHSV | Hydrogen Moles/100 Moles Feed |
|---|---|---|---|---|
| Carbon Bed | 190 | 130 | 1560 | 0 |
| $Pd/Al_2O_3$ Bed | 300 | 130 | 260 | 3 |

The effluent from this system was periodically sampled and analyzed for its isomerization effectiveness. The results are shown in the table below. For purposes of comparison, the results of a similar run without pretreatment are also shown in the table.

| Carbon Pretreatment | | No Pretreatment | |
|---|---|---|---|
| Time on Stream Hrs. | Isom. Eff. $C_4^= - 2/C_4^= - 1$ Ratio | Time on Stream Hrs. | Isom. Eff. $C_4^= - 2/C_4^= - 1$ Ratio |
| 4 | 0.9 | 4 | 0.9 |
| 5 | 0.9 | 5 | 0.9 |

The data in the table above show that the butene-2/butene-1 ratios obtained from the carbon pretreated run were significantly lower than those obtained from the alumina-pretreated runs of example 1. Moreover, there was no appreciable difference between the carbon-pretreated run and the non-pretreated run showing that the carbon-pretreatment was of little or no value with respect to enhancing the isomerization reaction of the system.

Example 3 (Comparison Run)

A molecular sieve pretreatment was used in an effort to improve the isomerization of a butene-1 feedstream. This feedstream was a synthetic one and designed to simulate a refinery stream. It was prepared by blending equal weight parts of a technical grade (95%) normal butane and a pure grade (99%) butene-1. To this mixture was also blended about 20 ppm of dimethyl disulfide. The composition of the synthetic blend is shown below.

| Component | Wt. % |
| --- | --- |
| $C_3$ | 0.3 |
| $iC_4$ | 0.5 |
| $nC_4$ | 48.8 |
| $C_4^= - 2$ | 0.05 |
| $C_4^= - 1$ | 50.0 |
| Neo $C_5$ | 0.1 |
| $iC_5$ | 0.15 |
| $nC_5$ | 0.1 |

The above described feed, having an initial butene-2/butene-1 ratio of about 0.001, was sequentially passed through a bed of molecular sieve as a pretreatment and then through a bed of the same $Pd/Al_2O_3$ catalyst described in example 1. The molecular sieve was a commercially available silica/alumina 13X mole sieve. The conditions were as follows:

|  | Temp. °F. | Press. psig | Space Rate GHSV | Hydrogen Moles/100 Moles Feed |
| --- | --- | --- | --- | --- |
| Mole Sieve bed | 190 | 130 | 1560 | 0 |
| $Pd/Al_2O_3$ bed | 260 | 130 | 260 | 3 |

The effluent from this system was periodically sampled and analyzed to determine its isomerization effectiveness. The results are shown in the table below. For purposes of comparison, the results of a similar run without pretreatment are also shown in the table.

| Mole Sieve Pretreatment | | No Pretreatment | |
| --- | --- | --- | --- |
| Time on Stream Hrs. | Isom. Eff. $C_4^= - 2/C_4^= - 1$ Ratio | Time on stream Hrs. | Isom. Eff. $C_4^= - 2/C_4^= - 1$ Ratio |
| 16.40 | 5.73 | 12.48 | 5.85 |
| 19.15 | 4.59 | 16.15 | 4.89 |
|  |  | 19.40 | 4.44 |

The data in the table above show that the butene-2/butene-1 ratios obtained from the mole sieve-pretreated run were significantly lower than those obtained from the alumina-pretreated run of example 1. Moreover, there was no appreciable difference between the mole sieve-pretreated run and the no-pretreatment run showing that the mole sieve-pretreatment was of little or no value with respect to enhancing the isomerization reaction of the system.

Reasonable variation and modification are possible within the scope of the foregoing disclosure and the appended claims to the invention the essence of which is that in a process for the isomerization of butene-1 to butene-2 the feedstream containing the butene-1 is treated to remove impurities, e.g., sulfur and arsenic, therefrom; the pretreatment involving a guard or pretreatment bed through which the feed is passed prior to contacting the same with a desired isomerization catalyst which is sensitive to impurities; and the pretreatment bed comprising activated alumina, which will remove such impurities.

I claim:

1. In the isomerization of isomerizable olefins in the presence of a catalyst the activity of which is adversely affected by an impurity such as sulfur or arsenic, the step of pretreating the feedstream by contacting the same at a temperature of the order of about 190° F. in a guard chamber or pretreatment bed containing an activated alumina contact mass adapted to remove from the feedstream the objectionable impurity.

2. A process according to claim 1 wherein butene-1 is isomerized to butene-2.

3. A process according to claim 2 wherein the catalyst bed comprises a supported Group VIII noble metal isomerization catalyst.

4. A process according to claim 1 wherein the catalyst is a palladium/alumina catalyst.

* * * * *